United States Patent [19]

Muller et al.

[11] Patent Number: 5,076,685

[45] Date of Patent: Dec. 31, 1991

[54] APPARATUS FOR OPHTHALMOLOGICAL LASER-THERAPY INSTRUMENTS

[75] Inventors: Dieter Muller, Konigsbronn; Jurgen Schwarz, Oberkochen, both of Fed. Rep. of Germany

[73] Assignee: Carl-Zeiss-Stiftung, Heidenheim/Brenz, Fed. Rep. of Germany

[21] Appl. No.: 546,391

[22] Filed: Jun. 29, 1990

[30] Foreign Application Priority Data

Jul. 4, 1989 [DE] Fed. Rep. of Germany ... 8908123[U]

[51] Int. Cl.$^5$ ............................................. A61B 3/10
[52] U.S. Cl. .................................... 351/221; 351/205
[58] Field of Search ............... 351/205, 211, 221, 214; 128/633, 745; 350/171

[56] References Cited

U.S. PATENT DOCUMENTS 4,582,405  4/1986  Muller et al. .

Primary Examiner—Rodney B. Bovernick
Attorney, Agent, or Firm—Eugene Stephens & Associates

[57] ABSTRACT

Apparatus for determining the focal plane of invisible laser-therapy radiation in ophthalmological instruments. A visible laser marking beam is split by simple means into four individual beams which share the instrument's optical path with the invisible laser radiation and are combined at the instrument's focal plane to form a single light spot.

7 Claims, 2 Drawing Sheets

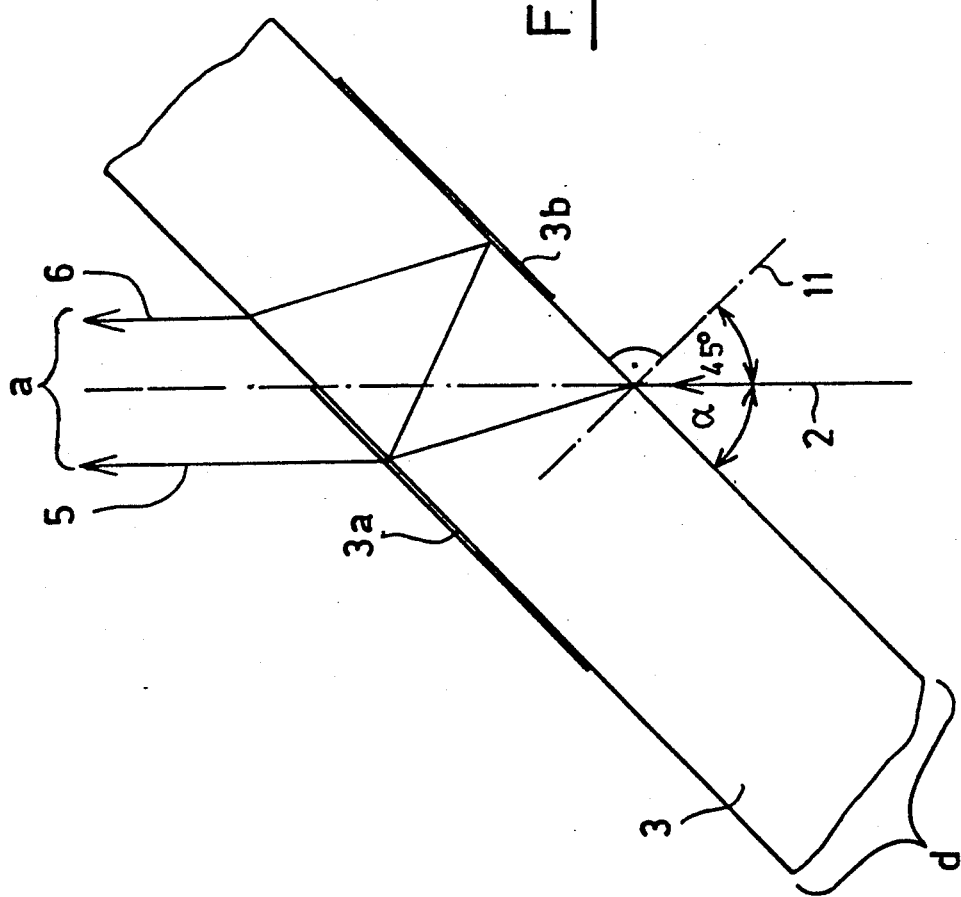

APPARATUS FOR OPHTHALMOLOGICAL LASER-THERAPY INSTRUMENTS

TECHNICAL FIELD

This invention relates to ophthalmological instruments used for invisible laser radiation therapy and, more particularly, to apparatus for determining the focal plane of invisible laser-therapy radiation in such instruments.

BACKGROUND

Ophthalmological laser-therapy instruments are used for operations in the front and middle regions of the eye. The laser radiation is conducted through the lens of the ophthalmological instrument and is focused on the eye of the patient. The source of the laser-therapy beam (sometimes identified as the instrument's "active" radiation) is generally a Nd-YAG laser which emits in the invisible region of the spectrum. Therefore, in order to check the focal plane of the active (i.e., therapy) radiation, the instrument has an observation ray path for viewing radiation in the visible region of the spectrum, and visible "marking" radiation is superimposed on the invisible therapy radiation. Such marking radiation is generally provided by a He-Ne laser which is arranged so that its focal plane coincides with the focal plane of the active radiation. By adjusting the focal plane of the marking beam, it is possible to determine and control the focal plane of the invisible active radiation being used for therapeutic purposes.

An instrument of this type is described in detail in U.S. Pat. No. 4,582,405, which also discloses a mechanism for determining the focal plane of the invisible active beam. This prior art mechanism divides the marking laser beam into two portions which are sequentially and alternately blocked. When the beam path is intercepted by a plane which is not identical with the focal plane of the instrument's radiation, the user has the impression that the marking radiation is blinking. This prior art focusing arrangement requires beam-widening means to be located at two places along the path of the marking beam, and it also requires occulting means for alternately blocking the respective portions of the marking beam.

SUMMARY OF THE INVENTION

The present invention provides simplified apparatus, as compared with the prior art, for determining the focal plane of an invisible medical laser beam by means of a visible laser beam. The remarkably simple apparatus of the invention comprises nothing more than two planoparallel glass plates positioned between the laser source for the marking beam and the instrument's beam-widening means, said plates being positioned so that they are at right angles (90°) to each other, with each plate being inclined, in the preferred embodiment, by 45° to the optical axis of the marking beam. The advantages obtained with the invention include (a) a reduction of the complexity and cost of the focusing system and, concomitant with this simplification, a drastic reduction in potentially disturbing light reflections from planes outside the focal plane, and (b) facilitating focus of the active beam on the eye of the patient, particularly on those areas outside of the optical axis of the eye in which the oblique incidence of the beam can result in astigmatic imaging.

DRAWINGS

FIG. 2 shows, in enlarged schematic form, the path of the marking laser beam through one of the planoparallel plates illustrated in FIG. 1.

DETAILED DESCRIPTION

Figure 1:
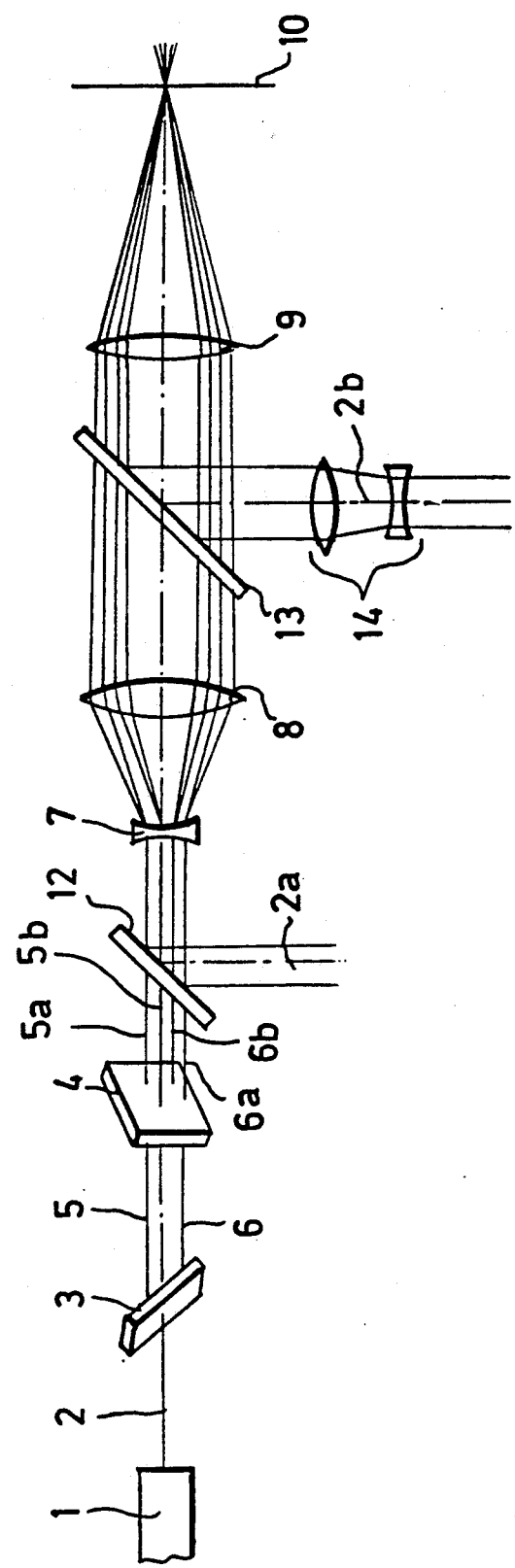
FIG. 1 is a simplified schematic diagram of an ophthalmological instrument including the invention showing, primarily, the path of the marking beam between the laser and the focusing plane of the instrument.

A preferred embodiment of the invention's apparatus for controlling the visible marking beam of an ophthalmological instrument is shown in simplified schematic form in FIG. 1. A He-Ne laser 1 is mounted with its optical axis aligned with the optical axis 2 of the instrument. A pair of planoparallel glass plates 3, 4 are each inclined at 45° to optical axis 2 so that they form an angle of 90° with each other. A beam emanating from laser 1 along optical axis 2 is split by glass plate 3 into two beams 5 and 6. When beams 5 and 6 impinge on glass plate 4, each is further split into the beams 5a, 5b and 6a, 6b. The multiply-split laser beam is passed through a beam-widening optical system comprising lenses 7 and 8, and then this marking laser beam is thereafter focused, by means of a lens 9, in the plane 10 of observation and treatment.

Special attention is called to the fact that the simplified schematic of FIG. 1 does not show the complete path of the instrument's Nd-YAG laser. It will be understood, however, that invisible radiation is emitted by a Nd-YAG laser along an optical path 2a before it is combined coaxially with the visible laser radiation by beam splitter plate 12. Similarly, FIG. 1 shows only a portion of a ray path 2b along which radiation from the plane of observation is reflected by splitter plate 13 and magnified by elements 14 for observation by the person using the instrument to operate on the eye of a patient. Those skilled in the art will appreciate that the omitted portions of these optical paths are similar to those used in presently-known instruments such as that disclosed in previously-mentioned U.S. Pat. No. 4,582,405.

FIG. 2 is an enlarged view of planoparallel plate 3, showing the splitting of a beam of visible laser radiation which is emitted along axis 2 and impinges on plate 3 at an angle of 45° to the normal 11.

The surfaces of plate 3 are preferably provided with a partially-reflecting layer 3a on which the incoming beam 2 impinges, and a totally-reflecting layer 3b positioned to reflect a portion of the incoming beam that is reflected from layer 3a. A portion of the incoming beam transmits through partially-reflecting layer 3a to emerge as beam 5, and the portion of the incoming beam that is reflected from layer 3a is fully reflected by layer 3b and emerges from plate 3 as beam 6. Preferably, incident beam 2 does not impinge on reflecting layer 3b; and beam 6, reflected from layer 3b, does not impinge on partially-reflecting layer 3a. Beam 6 exits from plate 3 at angle $\alpha$, which equals the angle between incoming beam 2 and plate 3.

The distance a between the individual beams 5 and 6 depends upon the thickness d and the index of refraction of plate 3, as well as upon the angle $\alpha$. By suitable dimensioning of these parameters for both plates 3 and 4, it is possible to have the four individual beams (5a, 5b, 6a, and 6b) emerge from glass plate 4 so that they are positioned symmetrically relative to optical axis 2. In this regard, it has been noted that planoparallel plates 3 and 4 are insensitive, within a range of ±0.5 mm, to displacement perpendicular to the optical axis.

When the four beams are focused by lens 9, a target beam having a diameter of about 15 μm can be obtained in the focal plane. However, upon defocusing, four light spots can be noted corresponding to the four individual beams, and these four light spots are merged into a single light spot in the focal plane when proper focus is achieved.

We claim:

1. Apparatus for determining the focal plane of invisible laser-therapy radiation in an ophthalmological instrument having an optical axis, an observation ray path for the visible region of the spectrum, a source of visible laser radiation for emitting a marking laser beam along said optical axis, and means for widening the beam of the laser radiation, said apparatus comprising two planoparallel glass plates positioned between the source of the marking laser beam and the beam-widening means, said plates forming an angle of 90° with each other and each of them being inclined to the optical axis and having reflecting layers positioned on opposite plane surfaces.

2. The apparatus according to claim 1 wherein said plates are each inclined by 45° to the optical axis.

3. In an ophthalmological instrument for emitting invisible laser radiation along an optical axis and focusing said invisible radiation on a treatment plane, said instrument having an observation ray path for visible radiation, a laser for emitting a marking beam of visible radiation along said axis and means for widening said laser radiation, the improvement for determining the focal plane of said invisible laser radiation comprising, two planoparallel glass plates, each plate having reflecting layers on its opposite plane surfaces, and each plate being positioned along and inclined to said axis between said marking beam laser and said beam-widening means, said plates being at right angles to each other, whereby said marking beam is split into two separate visible beams by a first one of said plates and each said separate visible beam is further split by the other of said plates so that said marking beam is divided into four spaced beams until said visible laser radiation is focused at said treatment plane.

4. The improvement according to claim 3 wherein said plates are positioned so that said four beams are spaced symmetrically to said optical axis.

5. The improvement according to claim 3 wherein said plates are inclined by 45° to said optical axis.

6. The improvement according to claim 3 wherein said reflecting layers include a partially-reflecting layer for splitting an incoming beam into a transmitted portion and a reflected portion, and a totally-reflecting layer positioned to receive and reflect said reflected portion.

7. The improvement according to claim 6 wherein said totally-reflecting layer is positioned clear of said incoming beam, and said partially-reflecting layer is positioned clear of a beam reflected by said totally-reflecting layer.

* * * * *